United States Patent [19]

Anderson

[11] Patent Number: 5,124,552
[45] Date of Patent: Jun. 23, 1992

[54] SENSOR AND METHOD FOR MEASURING WEB MOISTURE WITH OPTIMAL TEMPERATURE INSENSITIVITY OVER A WIDE BASIS WEIGHT RANGE

[75] Inventor: Leonard M. Anderson, San Jose, Calif.

[73] Assignee: Measurex Corporation, Cupertino, Calif.

[21] Appl. No.: 647,604

[22] Filed: Jan. 28, 1991

[51] Int. Cl.[5] ............................................. G01N 21/35
[52] U.S. Cl. ..................................... 250/339; 250/341
[58] Field of Search ....................... 250/341, 340, 339

[56] References Cited

U.S. PATENT DOCUMENTS

| | | | |
|---|---|---|---|
| 3,793,524 | 2/1974 | Howarth | 250/339 |
| 3,965,356 | 6/1976 | Howarth | 250/343 |
| 4,823,008 | 4/1989 | Sturm | 250/339 |
| 4,928,013 | 5/1990 | Howarth et al. | 250/339 |

FOREIGN PATENT DOCUMENTS

| | | | |
|---|---|---|---|
| 0279743 | 8/1988 | European Pat. Off. | 250/339 |
| 53-39194 | 10/1978 | Japan | 250/339 |
| 59-120940 | 7/1984 | Japan | 250/341 |

*Primary Examiner*—Constantine Hannaher
*Attorney, Agent, or Firm*—Spensley Horn Jubas & Lubitz

[57] ABSTRACT

An infrared web moisture sensor which is substantially temperature and basis weight insensitive comprises a source of infrared radiation for directing an infrared beam through the web and an infrared detecting unit on the other side of the web which measures the transmission of the infrared beam through the web at three separate wavelength regions. The transmission in the first wavelength region is primarily sensitive to the moisture content of the web. The transmissions in the second wavelength region is less sensitive to the moisture content. The transmission in the third wavelength region provides an indication of the web temperature. Temperature insensitivity is achieved by selecting the temperature response of a measurement band pass filter and a reference band pass filter based on the maximum basis weight and the maximum moisture content of the web and compensating for any remaining temperature sensitivity with a temperature correction band pass filter. Signals indicative of the transmission of infrared through the web in each of these regions are digitized and fed to the process control computer for the paper mill. The computer combines the values of the digitized signals, using an empirically derived equation, to produce a value indicative of the percentage of moisture in the web which value is not affected by changes in web temperature. The process control computer utilizes this result to control devices which selectively and moisture to portions of the web or selectively dry portions of the web, thereby producing a web having a desired moisture content profile.

20 Claims, 4 Drawing Sheets

SENSOR AND METHOD FOR MEASURING WEB MOISTURE WITH OPTIMAL TEMPERATURE INSENSITIVITY OVER A WIDE BASIS WEIGHT RANGE

BACKGROUND OF THE INVENTION (1) Field of the Invention

The present invention relates to the field of sensors for measuring physical properties of a web, and more particularly to a sensor and method for measuring moisture in a web by detecting the amount of infrared radiation in various wavelength regions after being transmitted through or reflected from the web. The measurement of the moisture content is optimally insensitive to the temperature, the basis weight and the composition of the web over a wide range of moisture, temperature and basis weights.

(2) Description of the Related Art

Paper is produced in a moving sheet called a "web." Because a paper web is produced from an aqueous suspension including wood pulp fibers, cotton fibers and various chemicals, the web initially contains a considerable amount of moisture. Most of this moisture is removed during the papermaking process. However, for a variety of reasons, it is desirable to maintain at least some moisture in the web. For example, if the web is too dry, it will tend to curl at the edges.

A paper web is normally dried by passing it around heated steel drying drums. However, this technique tends to dry the web unevenly. Such drying produces paper of uneven quality. Thus, various devices have been developed to moisten or dry only portions of the web. Typically, the moistening or drying occurs after the web has passed around the drying drums, to produce a web having a uniform moisture content. Of course, the paper mill operator, or the paper mill's process control computer, must know the moisture profile of the web before these moistening and drying devices can be used effectively Web moisture sensors have therefore been developed which scan back and forth across the cross-directional width of the web to determine its moisture content at various locations.

Water absorbs infrared radiation. Certain types of web moisture sensors take advantage of this phenomenon by directing a beam of infrared radiation at a web and measuring the intensity of the infrared beam after it passes through the web. The more moisture in a web, the greater the absorption of the infrared radiation in specific wavelength regions.

Some of these infrared moisture sensors use two infrared detectors with an infrared band pass filter positioned in front of each detector. The pass band of each filter is chosen so that each detector receives radiation in a narrow wavelength region of the infrared spectrum. One filter is chosen to pass infrared radiation in a region of strong absorption by the water in the web. Thus, the detector associated with this filter is sensitive primarily to the amount of water in the web. This first detector receives more infrared radiation when the web is dry and less infrared radiation when the web is moist.

A second band pass filter associated with a second detector is selected to pass infrared radiation in a region of the infrared spectrum where there is relatively little absorption by moisture. In this region, most of the absorption is due to the web fibers themselves, not to the moisture in the web. Thus, as the web weight per unit area (i.e., the "basis weight") increases, this second detector receives less infrared radiation. The output of this second detector is used to compensate the moisture measurements of the first detector for changes in the basis weight of the web. When the outputs from these two detectors are properly combined, these types of moisture sensors provide a measurement of the amount of moisture contained in the web or the percentage of moisture in the web, so that the moisture measurement is not affected by changes in the basis weight of the web.

However, the intensity of the transmitted infrared beam is not only dependent upon the moisture content and basis weight of the web. The absorption of infrared radiation by the moist web also varies with wavelength. The water and web fibers absorb certain wavelengths of the infrared spectrum more effectively than other wavelengths so that there are absorption peaks and valleys at various wavelengths along the spectrum. Moreover, these peaks and valleys shift to shorter wavelengths with increases in web temperature and to longer wavelengths with decreases in web temperature.

However, the previously described infrared moisture measuring devices fail to compensate for shifts in the infrared absorption spectrum resulting from changes in web temperature. Because on-line paper web temperatures may range from 10° C. to as high as 100° C., the moisture measurements of these devices are subject to significant error.

U.S. Pat. No. 4,928,013 to Howarth et al. ("Howarth") describes an infrared moisture sensor with two band pass filters which are selected to compensate for web temperature change. In this sensor, a first band pass filter, associated with a measure detector, is selected so that it is approximately centered around the infrared absorption peak for water, at about 1.93 microns. As the web temperature increases, the intensity of detected infrared radiation increases at the long wavelength side of the pass band filter, while an approximately equal decrease in the detected infrared occurs at the opposite short wavelength side of the pass band. With this technique, the total amount of infrared radiation reaching the measure detector is substantially insensitive to web temperature. A second band pass filter, associated with a reference detector, is selected so that it is in a region of the infrared spectrum which is predominantly absorbed by the web fibers The intensity of the infrared beam detected by the reference detector is primarily indicative of the basis weight of the web and is used to compensate for changes in basis weight.

The moisture sensor described in Howarth has the temperature insensitivity desired for the moisture measurements of some light weight paper, but may not achieve the degree of accuracy required by all customers, and more importantly, cannot achieve, the desired accuracy for heavier grades of paper sometimes encountered in paper manufacturing.

When band pass filters are manufactured there are inevitable variations in the exact band pass center wavelength and width, and for broader filters, in the shape of the transmission envelope. Thus, even with the lighter grades of paper, there is still some temperature sensitivity in a two band pass filter sensoi which cannot be removed and may affect the desired accuracy of the moisture measurements.

The measurement of the moisture content of heavier grades of paper with such a sensor has additional problems. Each grade of paper has its own characteristic transmission spectra. For example, paper usually contains between 2-12% moisture by weight. Thus, a heavier grade of paper will typically contain more moisture. However, as the amount of moisture increases, the water absorption peak increases in magnitude as well as broadens in the wavelength direction. Both of these effects tend to reduce the amount of radiation transmitted through the web. In fact, at the water absorption peak, the strong water and cellulose absorptions of the heavier grades of paper may effectively absorb nearly all of the radiation directed at the web from the infrared source. A narrow set of band pass filters which may be adequate for a light weight paper may be entirely inadequate in terms of transmitting the required amount of light through a heavier grade of paper.

Moreover, a moisture sensor with a set of filters which are nearly temperature insensitive for a lighter grade of paper may become very temperature sensitive as the shape of the transmission spectra changes with a heavier grade of paper, especially if the water absorption peak shifts partly or entirely outside the measurement region. Finally, even if the measure and reference filters are carefully selected there is still some residual temperature sensitivity when measuring heavier grades of paper which cannot be removed by a moisture sensor using a two band pass filter system.

Howarth also describes an infrared moisture sensor with a detecting unit which measures the transmission of the infrared beam through the web at three separate wavelength regions of the spectrum. The first band pass filter of the three filters passes infrared radiation having wavelengths within a slope of the absorption spectrum adjacent to the water absorption peak. Infrared radiation within this region is readily absorbed by water, but provides a stronger signal than if the pass band of the filter were centered directly over the water absorption peak, at about 1.93 microns. However, as a result, the output of the measure detector associated with this first filter becomes temperature sensitive.

A second band pass filter is selected to pass wavelengths in a region of the spectrum absorbed primarily by paper fibers. Therefore, the intensity of the infrared beam detected by the second detector is primarily indicative of the basis weight of the web. The output of the second detector is therefore used to correct the moisture measurement of the first detector for changes in basis weight.

A third band pass filter is selected to compensate for the temperature sensitivity of the first detector. The third filter passes a region of the spectrum where the water absorption of the infrared radiation varies rapidly with wavelength. For example, the third filter is preferably located on a slope of the absorption spectrum between a peak and a valley. Since the infrared spectrum for both water and paper fiber shifts to lower wavelengths with increases in web temperature, a third detector associated with the third filter is sensitive to web temperature. Since the third filter is located on a different portion of the infrared spectrum than the first filter, the output of the third detector will have a different temperature coefficient than the output of the first detector. Thus, the output of the third detector can be used to correct the moisture measurement of the first detector for the effects of changing web temperature.

However, the degree of compensation required by this technique to compensate for the temperature sensitivity of the measurement detector generates problems in certain contexts. For example, the third filter is typically selected to pass a region of the spectrum which is sensitive to not only the web temperature, but also to the composition and/or basis weight of the web. When the first and second filter are not selected to remove as much temperature sensitivity as possible, the high degree of temperature compensation required from the third detector may introduce significant dependence on the basis weight, ash, coating or pigment of the web. This dependence is normally removed by providing different calibration constants for different paper types.

A high degree of temperature compensation from the third detector introduces other sources of error. Howarth provides that the moisture of the web be calculated by combining the outputs from the three detectors in empirically derived equations. These equations combine values indicative of the amplitudes of each of the three detector signals to achieve a weighted average of these three values. The weighting coefficients of the equations, for example, C1 and C2, are dependent upon the width of the pass bands of each filter on the absorption spectrum. The coefficient values are chosen empirically to provide the weighted average of the detector signal values to minimize temperature and basis weight sensitivity.

The values for C1 and C2 are obtained by taking the readings of the three detector signals using samples of moisture-containing paper which are sealed between two plates of glass. To accomplish this, the glass-enclosed web is first heated. Then, measurements of the infrared penetration through the glass-enclosed web are made periodically as the temperature of the glass-enclosed web decreases.

In some applications, the amount of compensation needed for temperature insensitivity in glass-enclosed sample tests is different from that needed for on-line measurement. It would be highly desirable if the calibration constants obtained on samples at temperature around 22° C. were correct for on-line measurements, even for paper in a very strongly non-equilibrium state at around 100° C. As a practical matter, however, this method of calibrating the temperature compensation by glass-enclosed samples provides different values for the constant C1 than that required for on-line measurements. This is presumably due to the non-equilibrium condition of the paper on-line at a high temperature having a different affect on the absorption, for example, at 1.6 microns than on the absorption at 1.9 microns. This different value for the calibration constant can introduces an additional source of error in the moisture measurements. The high degree of compensation required exacerbates this source of error.

Thus, there is a need for a moisture sensor which can overcome these types of problems and accurately determine the moisture content of the web in a manner which is optimally insensitive to the temperature, the basis weight and the composition of the web over a wide range of moisture, temperature and basis weights.

SUMMARY OF THE INVENTION

The present invention includes a sensor, device and a method for determining the moisture content of a web by detecting the amount of infrared radiation transmitted through the web, or reflected from the web, in three separate wavelength regions of the infrared spectrum. Temperature insensitivity is achieved by carefully selecting the temperature response of a first band pass filter, the measurement filter, and a second band pass filter, the reference filter, based on the maximum basis weight and maximum moisture content of the web and further compensating for any remaining temperature sensitivity with a third band pass filter, the temperature correction filter.

The sensor, device and method are primarily, but not exclusively, intended for on-line moisture measurements of a moving paper web during papermaking. In this situation, the moisture sensor may be scanned back and forth across the cross-directional width of the moving web, thereby providing a measurement of the moisture content at various positions along the length and width of the web. Signal processing circuitry and computer software associated with the sensor may further compensate the moisture measurement for changes in the basis weight and/or web temperature.

The moisture sensor includes a source of infrared radiation for transmitting a beam of infrared radiation through a moving web. As the beam passes through the web, the water in the web and the primary constituent of the web (e.g., web fibers) absorb a portion of the infrared beam. The infrared beam contains a broad range of wavelengths. However, infrared radiation at certain wavelengths is preferentially absorbed by the moisture-containing web.

The moisture sensor also includes an infrared receiver. The receiver is positioned on the opposite side of the web from the infrared source and measures the intensity of the transmitted infrared radiation in first, second and third separate wavelength regions of the spectrum. The receiver may comprise a beam splitter and three infrared detectors. The beam splitter directs a portion of the infrared beam at each of the three detectors. A separate infrared band pass filter is positioned before each detector. In this way, each of the detectors detect the intensity of the infrared radiation falling within the wavelength region of the pass band of the associated filter.

In one embodiment, the first band pass filter is selected to pass infrared radiation in a first region of the spectrum around the absorption peak for water in the web such that the infrared radiation detected in the first region is substantially insensitive to the web temperature. The intensity of the infrared radiation detected by the associated first detector is indicative of the moisture content of the web.

In the same embodiment, a second band pass filter is selected to pass infrared radiation in a second region of the spectrum that is less sensitive to the water in the web than the first region and substantially insensitive to the web temperature. The second band pass filter also passes radiation in a region of the spectrum absorbed by the primary constituent of the web (e.g., paper fibers). Therefore, the intensity of the infrared radiation detected by the associated second detector is indicative of the basis weight of the web. By selecting the first and second band pass filters in this way, the moisture measurements will be substantially insensitive to changes in the temperature and basis weight of a light or medium weight web.

Nonetheless, a third band pass filter is selected to pass a third region of the infrared spectrum which is temperature sensitive to compensate for any remaining temperature sensitivity and/or undesired variations in the first and second band pass filters. Since the pass band of this third filter is located on a different portion of the absorption spectrum than the first band pass filter, the output from this detector will have a different temperature coefficient than the output of the first detector. Therefore, the output of this third detector may be used to correct the web moisture measurement of the first detector and second detectors for the effects of changing web temperature on the infrared absorption characteristics of water.

In another embodiment, relating to medium and heavier weight paper products, the first band pass filter again passes infrared radiation in a first region around the absorption peak for water in the web to minimize temperature sensitivity. However, the strong water and cellulose absorptions of heavier grades of paper in the first region may absorb nearly all of the infrared radiation directed at the web from the infrared source. Thus, the invention provides a broader first band pass filter than the previous embodiment to pass an adequate amount of infrared radiation. By broadening the first band pass filter, however, the first region becomes sensitive to changes in the web temperature.

To compensate for this temperature sensitivity, a second band pass filter is selected to pass a second region of the infrared spectrum which is less sensitive to the water in the web than the first region and sensitive to the web temperature to substantially the same degree as the first region. The second band pass filter also passes radiation in the region of the spectrum absorbed by the primary constituent of the web. Thus, the intensity of the infrared beam detected by the detector behind this second filter is indicative of the basis weight of the web. As discussed below, the output of this detector behind the second filter is then used to correct the moisture measurement of the first detector for changes in the basis weight and temperature of the web. Thus, the present invention can provide a signal indicative of the moisture weight in the web, irrespective of changes in basis weight and temperature.

As described above, the third band pass filter is selected to pass a part of the infrared spectrum which is temperature sensitive to compensate for any remaining temperature sensitivity and/or undesired variations in the first and second band pass filters.

According to the present invention, the outputs from the three detectors may then be combined, in an empirically determined formula, to yield an output which is indicative of the moisture content of the web. As previously explained, the output of one of the three detectors in the receiver of the present invention will be primarily affected by the amount of moisture in the web between the infrared beam source and the receiver. But this detector alone cannot give an accurate indication of the percentage of moisture in the web since this detector will receive less infrared radiation either (1) when the percentage of moisture increases or (2) when the percentage of moisture remains constant but the web basis weight increases. The amount of infrared radiation reaching this first detector also will be affected by shifts in the absorption spectrum caused by changes in web temperature.

By monitoring the output of only this one detector, the paper mill operator (or the mill's process control computer) would be unable to differentiate between changes in the moisture content of the sheet, changes in basis weight and changes in web temperature. However, the filters associated with the second and third detectors are chosen so that the output of the second detector in the receiver varies with changes in basis weight, while the output of the third detector varies with changes in web temperature. By combining the output from the first detector in a weighted average with the output of the second and third detectors, the resulting combination can be made to indicate the amount of moisture in the web so that this indication is independent of both changes in web temperature and changes in basis weight.

The coefficients used in the formula for combining the outputs from the three detectors will depend, for example, upon the exact location of the band pass filters along the absorption spectrum and the width of the pass bands of these filters. The exact values for these coefficients can be determined empirically by measuring the outputs from each of the three detectors at a plurality of temperatures and basis weights and then choosing coefficients for the formula combining these outputs which minimize the temperature sensitivity of the resulting weighted average of the outputs.

Rather than using three separate infrared detectors and a beam splitter to create three separate beams, the receiver half of the moisture sensor can be constructed using a single infrared detector and a mechanism for sequentially positioning each of the three band pass filters discussed above in front of the single detector. With this configuration, the output from the detector is determined at different times corresponding to the times when each of the three filters is in the path of the infrared beam. The outputs of the detector, corresponding to the times when each of the three filters is positioned before the detector, is then combined in the same manner as explained above in connection with the three detector embodiment to yield a moisture measurement which is insensitive to changes in web temperature.

This technique for measuring the moisture contained in a web can also be used with a single sided infrared reflectance sensor. As described earlier, the temperature insensitivity can be achieved by carefully selecting the temperature response of a first band pass filter, the measurement filter, and a second band pass filter, the reference filter, based on the maximum basis weight and maximum moisture content of the web and further compensating for any remaining temperature sensitivity with a third band pass filter, the temperature correction filter. Thus, the criteria for selecting the detected regions is the same as that described earlier for the infrared transmission sensor.

U.S. Pat. No. 3,965,356 to Howarth, which is incorporated herein by reference, describes a single sided reflectance sensor that can use the principles of the present invention. For the sake of simplicity, the invention will be described in connection with an infrared transmission sensor. However, it is understood that the present invention can also be embodied in a single sided reflectance sensor.

BRIEF DESCRIPTION OF THE DRAWINGS

The foregoing objects, features and advantages of the invention will become more apparent from the following detailed description of the preferred embodiments taken in conjunction with accompanying drawings, in which.

DETAILED DESCRIPTION OF THE PREFERRED EMBODIMENTS

The following description is the best contemplated mode of carrying out the invention. This description is made for the purpose of illustrating the general principles of the invention and should not be taken in a limiting sense. The scope of the invention is best determined by reference to the appended claims. In the accompanying drawings, like numerals designate like parts.

Figure 1:
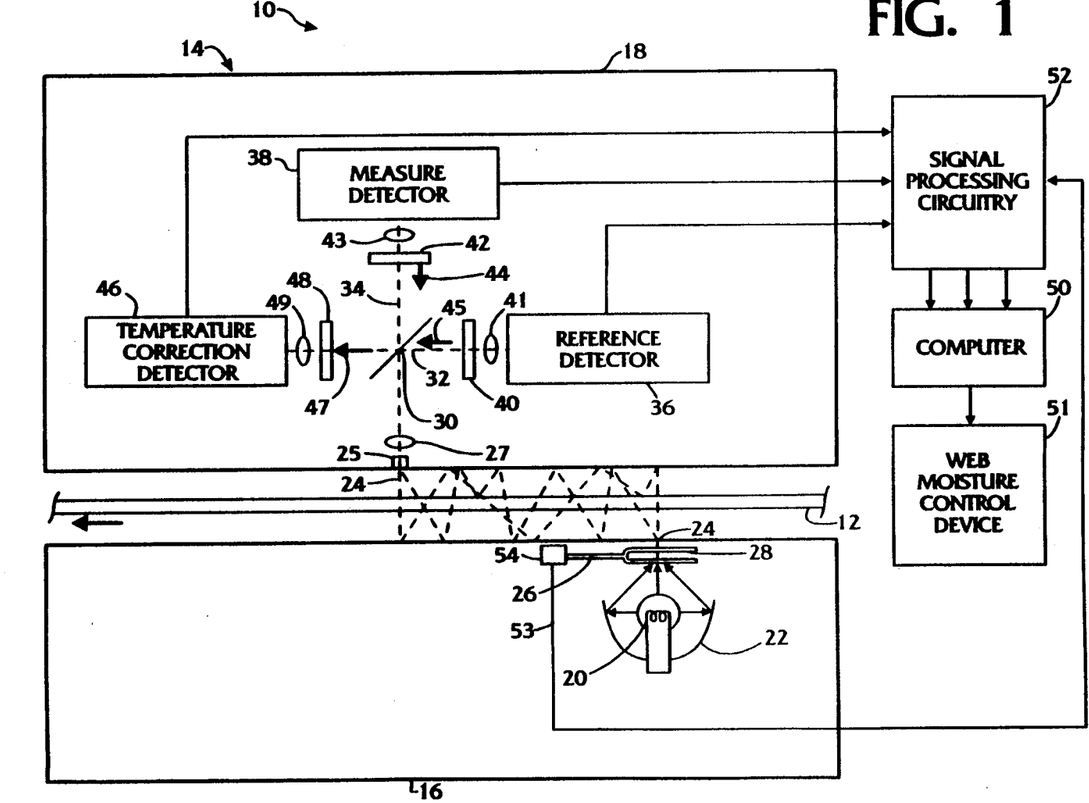
FIG. 1 is a schematic elevation view illustrating a temperature compensating moisture sensor constructed according to the present invention.

The invention includes the infrared moisture device 10 illustrated in FIG. 1. The device is used to measure the moisture content of a paper web 12 and to automatically compensate this measurement both for changes in the basis weight and temperature of the web 12. To accomplish this measurement, the device of FIG. 1 uses a sensor 14 which may be thought of as having two halves, a source half 16 and a receiver half 18, located on opposite sides of the web 12.

The infrared source 16 uses an incandescent lamp 20 and an elliptical reflector 22 to direct a beam of infrared radiation 24 through the web 12 It is preferred, but not necessary to the invention, that the amount of infrared radiation exiting the source 16 and impinging upon the web 12 be modulated at a known frequency. This modulation may be accomplished by any one of several devices. For example, as illustrated in FIG. 1, the tines 28 of a tuning fork 26 may be disposed in the path of the infrared beam 24. The vibrating tines 28 modulate the infrared beam 24 as the tines 28 move alternatively into and out of the path of the beam 24. Alternatively, an opaque disk (not shown) having a plurality of evenly spaced radial slots may be rotated in the path of the beam so that the beam is alternately transmitted through the slots and blocked by the opaque portions of the disk. With either device, the beam 24 is modulated at a known frequency. The reason for modulating the beam is explained below.

In the embodiment illustrated in FIG. 1, it is also preferred, but not necessary to the invention, that the beam 24 be reflected back and forth between the source 16 and receiver 18 sides of the sensor 14 before entering the receiver 18. Reflecting the beam 24 repeatedly between the source 16 and receiver 18 so that the beam 24 passes a plurality of times through the web 12 provides certain advantages when measuring the moisture content of very light grades of paper, such as tissue, and very heavy paper grades. This technique and the advantages of such multiple reflections are more fully discussed in U.S. Pat. No. 3,793,524 to Howarth incorporated herein by reference. Alternatively, the beam 24 may be directed in a single straight line from the source 16 to the receiver 18 so that the beam 24 only passes once through the web 12.

The receiver 18 includes a light pipe 25 which guides the beam 24 to a lens 27 located between the light pipe 25 and a beam splitter 30. The beam splitter 30 splits the beam 24 into two separate beams 32 and 34. Each of these beams is directed at separate band pass filters 40 and 42 positioned in their respective path and immediately before lenses 41 and 43, respectively. The lens 27 casts an image of the beam 24 emerging from the surface of the light pipe 25 onto the center of each of the lenses 41 and 43. The lenses 41 and 43 are used to focus the maximum amount of infrared radiation on lead sulfide detectors 36 and 38. Each filter 40 and 42 is selected so that it passes infrared radiation in a separate region of the infrared spectrum. Infrared radiation not within the pass band of the filters 40 and 42 is reflected by these filters back to the beam splitter 30 (as shown at reference numerals 45 and 44) and thus does not reach the reference or measure detectors 36 and 38. However, the reflected beam 44 impinges upon the beam splitter 30 and the beam splitter 30 directs some of the beam 44 to a third filter 48. Moreover, some of the infrared beam 32 is reflected from filter 40 (as shown at 45), where it passes through the beam splitter 30 to combine with the portion of the beam 44 reflected by the beam splitter 30 toward filter 48. The combined beam is shown by reference numeral 47. A lens 49 is used to focus the maximum amount of infrared radiation on lead sulfide detector 46. Thus, with the moisture sensor 14 of the invention, a single beam 24 enters the receiver 18, but the optics within the receiver 18 split up the beam 24 into three separate beams 32, 34 and 47, each detected by an associated infrared detector 36, 38 and 46.

The pass band of each of the three filters 40, 42 and 48 is selected so that the wavelength region of radiation reaching each of the three detectors 36, 38 and 46, and thus the signal from each detector, is affected by the basis weight, the amount of moisture and the temperature of the web, respectively. Using these three signals, and the equations discussed below, a process control computer 50 periodically computes the moisture content of the web 12. Furthermore, by scanning the sensor 14 back and forth in the cross-direction of a moving web 12 as the web 12 is being produced, the invention can provide signals indicative of the moisture content of the web 12 at various locations across the length and width of the web 12. These moisture measurements can then be used to selectively control various well known web moisture control devices 51 for increasing or decreasing the moisture content of portions of the web 12, thereby providing a web 12 having a uniform moisture content, if desired, across its width and along its length.

Based on the moisture measurements, a web moisture correction can be accomplished manually. However, many modern paper mills are highly automated. In these paper mills, the signals produced by the sensor 14 of the present invention are preferably fed to a process control computer 50 which computes the web moisture profile using the signals from the three infrared detectors 36, 38 and 46 and then, based on this computation, selectively activates one or more known devices 51 for altering the moisture content of certain portions of the web 12. Many such devices 51 for altering the web moisture profile exist, including such devices as selectively controllable water showers for increasing the moisture content of select cross-directional sections of the web 12 and/or infrared heaters for selectively drying such sections of the web 12.

Figure 2:
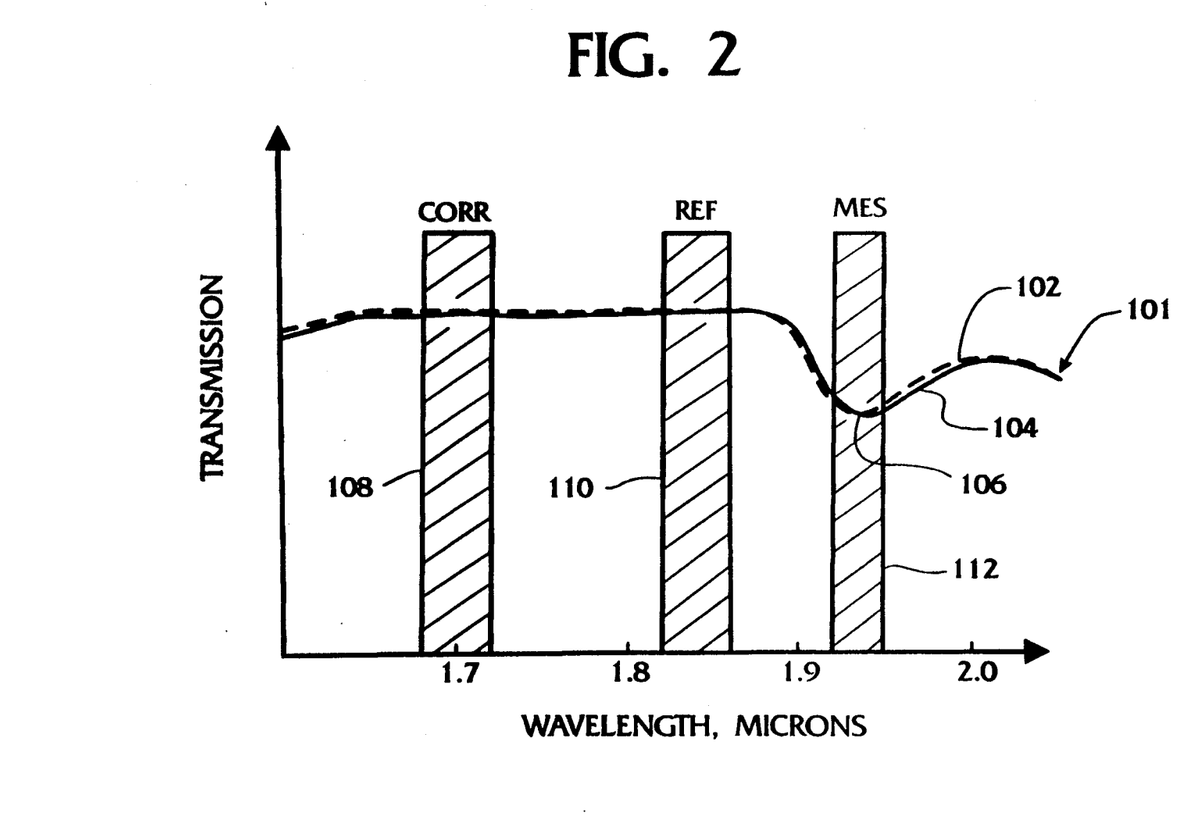
FIG. 2 illustrates infrared transmission spectra of a light weight paper web, containing moisture, at two different temperatures with an indication of appropriate detected measure, reference and temperature correction wavelength regions.

FIG. 2 illustrates the infrared transmission spectrum 101 for a light weight paper web, e.g., 70 grams/meter$^2$ (gsm), containing moisture, at a temperature of approximately 22° C. and of 60° C. The cross-hatched areas denoted MES, REF, and CORR indicate the wavelength regions detected by the measure detector 38, reference detector 36 and temperature correction detector 46. To obtain the infrared spectrum, the paper web was sealed between two plates of glass to prevent loss of moisture during heating. The glass served, not only to maintain constant moisture values within the paper web during the measurements, but also to provide a thermal mass which maintained the web temperature to make possible measurements at temperatures above the ambient or lower temperature To accomplish this, the glass-enclosed web is first heated. Then measurements of the infrared penetration through the glass enclosing the web are made at the higher and lower temperature.

The infrared absorption spectrum of water and paper is peculiar in that the absorption characteristics of the entire spectrum shift to shorter wavelengths as the web temperature is increased and to longer wavelengths as the web temperature decreases. The infrared spectra of the light weight paper web at the higher temperature is shown by the dashed line 102. The infrared spectra at the higher temperature is shown by the solid line 104. Of course, the infrared spectra 102 of the web at the higher temperature has approximately the same absorption characteristic as the lower temperature web, but at shorter wavelengths.

Absorption at the shorter wavelengths of the spectrum, i.e., below about 1.9 microns, is dependent upon absorption by the paper web fibers. Conversely, at the longer wavelength end of the spectrum, above approximately 1.9 microns, water is more efficient at absorbing infrared radiation than the web fibers. Hence, the longer wavelength portion of the spectrum is prominently affected by the moisture content of the web. For example, the absorption peak for water (corresponding to minimum infrared transmission) may occur at a wavelength of approximately 1.93 microns. Nevertheless, the entire infrared spectrum is absorbed, at least to some extent, by water in the web.

For a light weight paper web, an infrared band pass filter 42 (FIG. 1) associated with a measure detector 38 may have its pass band 112 approximately centered around the water absorption peak 106, for example, at approximately 1.93 microns. For this purpose, we may use a band pass filter 42 (FIG. 1) with a range from 1.920 to 1.950 microns, the lower and upper wavelengths at which the transmission reaches half that which is achieved at the transmission peak. In this way, as the web temperature increases, the intensity of detected infrared radiation in the MES region increases at the long wavelength side of the region, while an approximately equal decrease in detected infrared radiation occurs at the opposite short wavelength side of the region. With this technique, the total amount of infrared radiation reaching the measure detector 38 is strongly sensitive to the moisture content and substantially insensitive to web temperature. Thus, the signal from measure detector 38 (the "MES" signal) provides a rough measurement of the web moisture content which is substantially temperature insensitive.

As mentioned earlier, the basis weight also affects the infrared absorption spectrum. To provide a signal which is sensitive to the basis weight, a band pass filter 40 is positioned before a reference detector 36. The filter 40 has its pass band 110 defining a REF region which is less sensitive to water and substantially insensitive to the web temperature. For example, a filter with a bandpass range from 1.820 to 1.860 microns (normal incidence) has both of these characteristics. Because the pass band 110 of the filter 40 is less than 1.9 microns, it is sensitive to the basis weight of the web 12. Accordingly, as the basis weight increases, the amount of infrared radiation passing through the web decreases. Thus, the signal from detector 36 (the "REF" signal) provides a rough measurement of the basis weight of the web. By selecting the band pass filters 42 and 40 in this way, the ratio of the REF/MES signals is substantially insensitive to the web temperature.

Because the ratio of the REF/MES signals may still be sensitive to the web temperature, the invention provides a temperature correction detector 46 (FIG. 1) for temperature correction with an associated infrared band pass filter 48. The signal from this temperature correction detector 46 (the "CORR" signal) may be used to further correct the moisture measurement of the sensor 14 for the effects of varying web temperature. The pass band 108 chosen for this filter 48 passes radiation in a region of the transmission spectrum 101 so that the amplitude of the signal from the temperature correction detector 46 is sensitive to changes in the web temperature. The changes in the CORR signal from the temperature correction detector are used to compensate for the temperature induced changes in the MES signal.

A preferred position for the detected CORR region or pass band 108 of this filter is shown in FIG. 2. For example, a band pass filter of 1.680 to 1.720 microns passes a region of the infrared spectrum where favorable temperature correction has been achieved for light weight paper.

Figure 3:
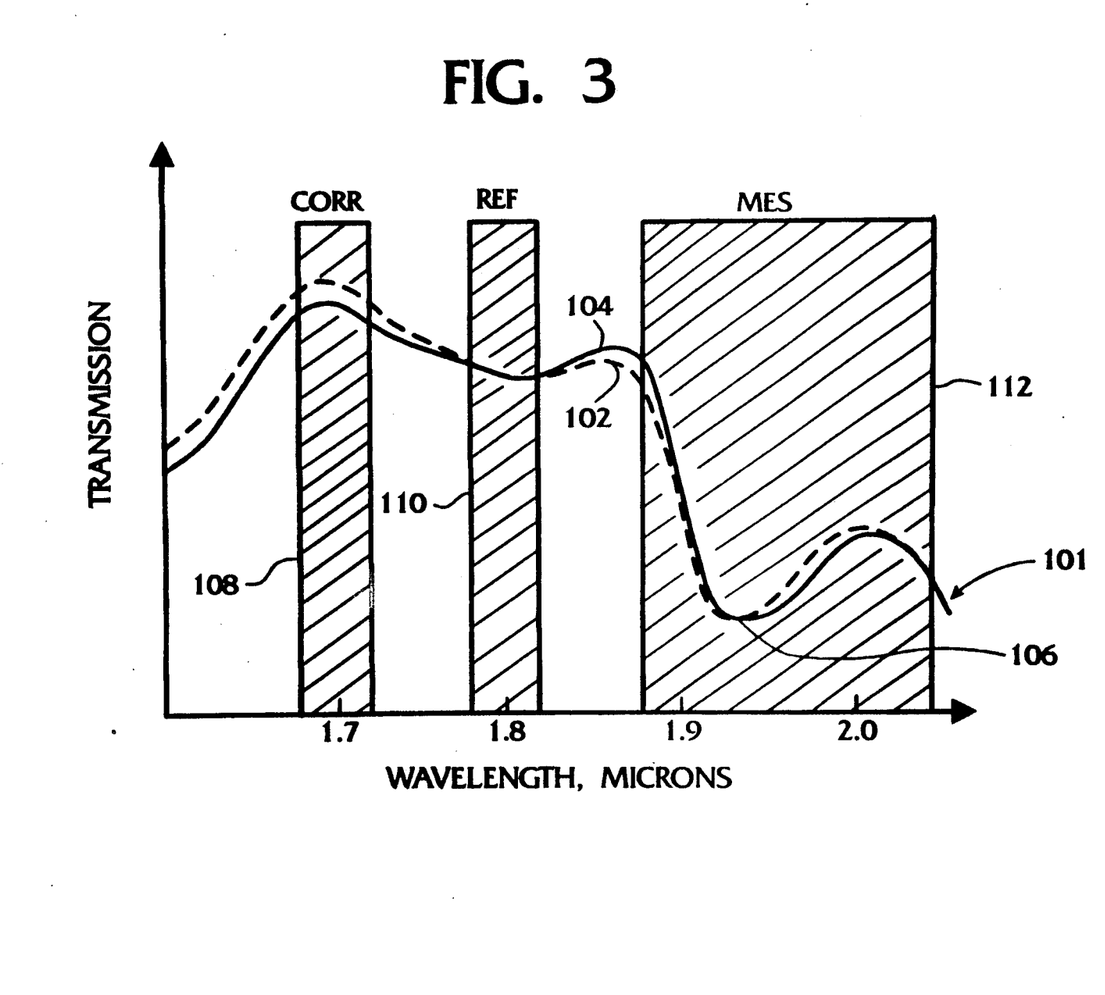
FIG. 3 illustrates infrared transmission spectra of a medium weight paper web, containing moisture, at two different temperatures with an indication of appropriate detected measure, reference and temperature correction wavelength regions.

FIG. 3 illustrates the infrared transmission spectrum 101 for a medium weight paper web (e.g., a 205 gsm liner board), containing moisture, at a temperature of approximately 22° C. and of 60° C. The infrared spectrum of the web at the higher temperature is shown by the dashed line 102. The infrared spectrum of the web at the lower temperature is shown by the solid line 104. To obtain the infrared spectrum, the paper web was sealed between two plates of glass to prevent loss of moisture during heating. Then measurements of the infrared penetration through the glass enclosed sheets were made at the higher and lower temperature. The cross-hatched areas denoted MES, REF, and CORR again illustrate the separate wavelength regions to be passed through the respective filters and detected.

As mentioned earlier, a heavier weight paper product typically contains more moisture than a light weight paper. As the amount of moisture increases, the water absorption peak increases in magnitude as well as broadens in the wavelength direction. As illustrated by FIG. 3, both of these effects tend to reduce the amount of radiation transmitted through the web. In fact, at and around the water absorption peak, the strong water and cellulose absorptions of a heavier grades of paper may effectively absorb much of the infrared radiation directed at the web from the infrared source. Thus, the narrow band pass filter as used for the light weight paper discussed earlier may be entirely inadequate in terms of passing the required amount of radiation to the detector.

Rather than selecting such a narrow band pass filter to pass infrared radiation in a region adjacent to the water absorption peak, the invention overcomes the problem of relatively low transmission by providing a relatively broad band pass filter around the water absorption peak. This also minimizes temperature sensitivity by ensuring that the integrated areas beneath the infrared transmission spectrum for a wide range of temperatures remain roughly equal and that the water absorption peak remains within the filter envelope.

For this medium weight paper web, an infrared band pass filter 42 (FIG. 1) associated with the measure detector 38 may have its pass band 112 around the water absorption peak 106. For this purpose, we may use a band pass filter 42 (FIG. 1) with a range from 1.880 to 2.050 microns (at normal incidence).

In this way, as the web temperature increases, the absorption peak remains within the pass band 112, and the intensity of detected infrared radiation in the MES region increases at the long wavelength side of the region, while an approximately equal decrease in detected infrared radiation occurs at the opposite short wavelength side of the region. With this technique, the total amount of infrared radiation reaching the measure detector 38 is strongly sensitive to the moisture content and substantially insensitive to web temperature. This is because total amount of infrared radiation reaching the measure detector 38 is proportional to the integrated area underneath the transmission curve. Thus, the signal from measure detector 38 (the "MES" signal) provides a rough measurement of the web moisture content which is substantially temperature insensitive.

As previously mentioned, the infrared absorption spectrum is also affected by the basis weight of the web 12. To provide a signal dependent upon the basis weight of the web 12, a band pass filter 40 is positioned before a reference detector 36. As shown by FIG. 3, this filter 40 has its pass band 110 at a wavelength region which is less sensitive to water and substantially insensitive to the web temperature. For example, a band pass filter with a range from 1.780 to 1.820 microns (normal incidence) has both of these characteristics. Because the pass band 110 of this filter 40 is less than 1.9 microns, it is also sensitive to the basis weight of the web 12. Accordingly, as the web basis weight increases, the amount of infrared radiation which passes through the web 12 decreases Thus, the signal from this detector 36 (the "REF" signal) provides a rough measurement of the basis weight of the web. With the band pass filters chosen in this way, the ratio of the REF/MES signals is substantially insensitive to the web temperature.

As in the measurement of the light weight paper, because the ratio of the REF/MES signals may still be sensitive to the web temperature, the invention provides a temperature correction detector 46 (FIG. 1) for temperature correction with an associated infrared band pass filter 48. The signal from this temperature correction detector 46 (the "CORR" signal) may be used to further correct the moisture measurement of the sensor 14 for the effects of varying web temperature. The pass band 108 chosen for this filter 48 passes radiation in a region of the transmission spectrum 101 so that the amplitude of the signal from the temperature correction detector 46 is sensitive to changes in the web temperature. The changes in the CORR signal from the temperature correction detector are used to compensate for the temperature induced changes in the MES signal.

A preferred position for the detected CORR region or pass band 108 of this filter is shown in FIG. 2. For example, a band pass filter of 1.680 to 1.720 microns passes a region of the infrared spectrum where favorable temperature correction has been achieved for medium weight paper.

Figure 4:
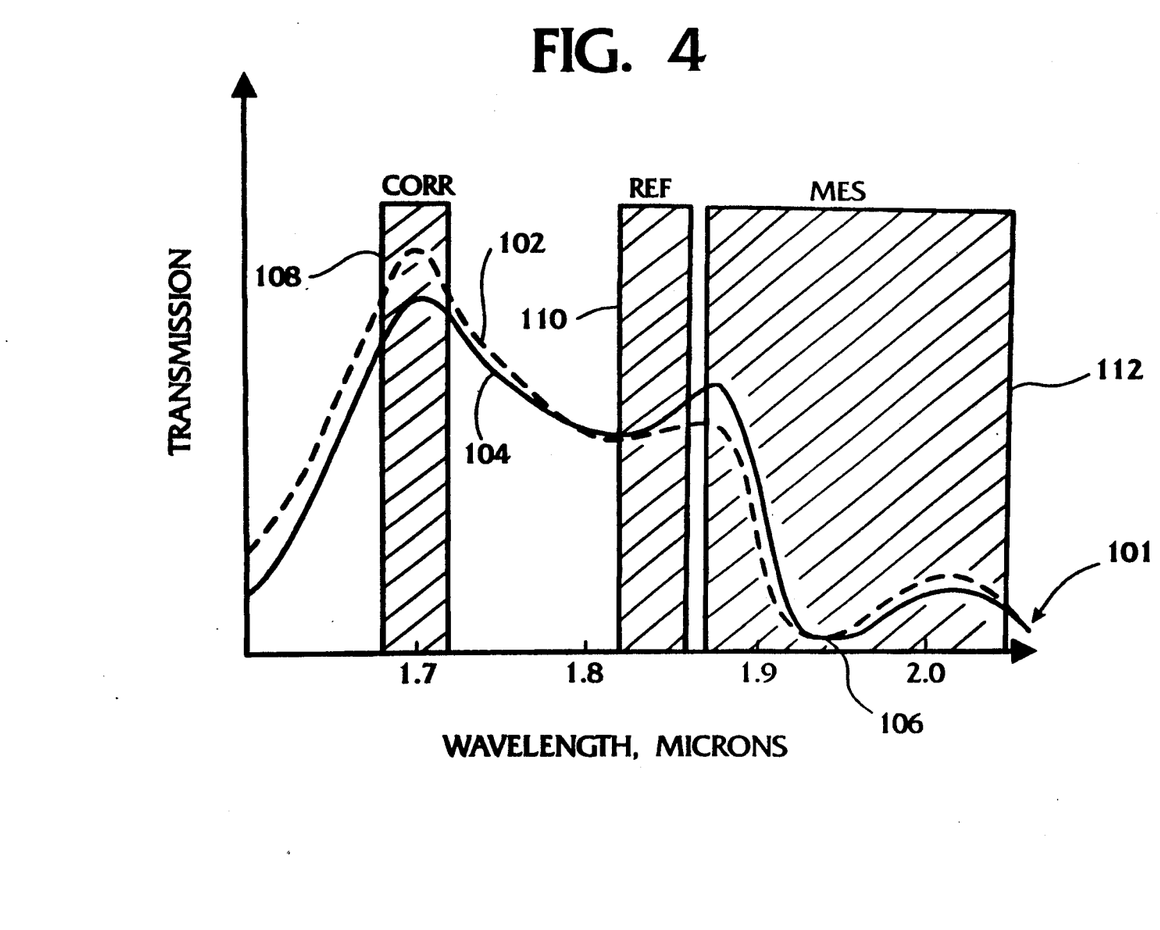
FIG. 4 illustrates infrared transmission spectra of a heavy weight paper web, containing moisture, at two different temperatures with an indication of appropriate detected measure, reference and temperature correction wavelength regions.

FIG. 4 illustrates the infrared transmission spectrum 101 for a heavy weight paper web (e.g., a 345 gsm liner board), containing moisture, at a temperature of approximately 22° C. and of 60° C. As in FIGS. 2-3, the infrared spectrum of the web at the higher temperature is shown by the dashed line 102. The infrared spectrum of the web at the lower temperature is again shown by the solid line 104. To obtain the infrared spectrum, the paper web was again sealed between two plates of glass to prevent loss of moisture during heating. Then measurements of the infrared penetration through the glass-enclosed sheets are made at the higher temperature and at the ambient or room temperature. The cross-hatched areas designated CORR, REF and MES, again illustrate the separate wavelength regions to be passed through the three filters and detected.

As mentioned earlier, a heavier grade of paper typically contains more moisture than a lighter weight paper. As the amount of moisture increases even more than that contained in a medium weight paper web, the water absorption peak increases in magnitude as well as broadens in the wavelength direction even more. As illustrated by FIG. 4, both of these effects tend to further reduce the amount of radiation transmitted through the web. In fact, around the water absorption peak, the strong water and cellulose absorptions of the heavier grades of paper absorb much of the infrared radiation directed at the web from the infrared source. Thus, a narrow band pass filter as specified for the light weight paper, or even the broader band pass filter specified for the medium weight paper may be inadequate to pass the required amount of radiation to the detector.

The invention overcomes the problem of relatively low transmission by providing an even broader band pass filter around the water absorption peak than in the situations illustrated in FIGS. 2 and 3. This also minimizes temperature sensitivity by ensuring the water absorption peak remains within the filter envelope.

For this heavy weight paper web, an infrared band pass filter 42 (FIG. 1) associated with the measure detector 38 may have its pass band 112 around the water absorption peak 106. For this purpose, we may use a band pass filter 42 (FIG. 1) with a range from 1.870 to 2.050 microns (at normal incidence).

In this way, as the web temperature increases the peak remains within the pass band, and the intensity of the infrared radiation increases on the long wavelength half of the filter 42, while a decrease in the intensity of the infrared radiation occurs at the opposite short wavelength half of the filter 42. However, this technique does not result in temperature insensitivity, because the total amount of infrared radiation reaching the measure detector 38 is not substantially equal for the high and low temperatures. Thus, the measurement detector 38 is not only strongly dependent upon the moisture content of the web 12, but also sensitive to the web temperature. Thus, the signal from measure detector 38 (the "MES" signal) provides a measurement of the web moisture content which is temperature sensitive.

As previously mentioned, the infrared absorption spectrum is also affected by the basis weight of the web 12. To provide a signal sensitive to the basis weight of the web 12, a band pass filter 40 is positioned before a reference detector 36. To compensate for the temperature sensitivity of the MES signal, the filter 40 has its pass band 110 defining a REF region which is less sensitive to the water in the web than the MES region surrounding the water absorption peak, but sensitive to the web temperature to substantially the same degree as the MES region. For example, a filter with a bandpass range from 1.820 to 1.860 microns (normal incidence) has these characteristics.

Because the pass band 110 of this filter 40 is less than 1.9 microns, it is also sensitive to the basis weight of the web 12. Accordingly, as the web basis weight increases, the amount of infrared radiation which passes through the web 12 decreases. Thus, the signal from this detector 36 (the "REF" signal) provides a rough measurement of the basis weight of the web. With the band pass filters chosen in this way, the temperature sensitivity of the ratio of the REF/MES signals is minimized.

As described above, a temperature correction band pass filter with its pass band 108 is selected to pass a wavelength region which is temperature sensitive to compensate for any remaining temperature sensitivity and/or undesired variations in the measure and reference band pass filters.

Table 1 gives the appropriate band pass filters for basis weights of up to 400 gsm. Band pass ranges are expressed as the lower and upper wavelengths at which the transmission reaches half that which is achieved at the transmission peak.

TABLE 1

| Maximum Basis Weight gsm | Maximum Water Weight gsm | MES Filter microns | | REF Filter microns | | CORR Filter microns | |
|---|---|---|---|---|---|---|---|
| | | lower | upper | lower | upper | lower | upper |
| 70  | 7  | 1.920 | 1.950 | 1.820 | 1.860 | 1.680 | 1.720 |
| 150 | 15 | 1.900 | 2.000 | 1.780 | 1.820 | 1.680 | 1.720 |
| 250 | 25 | 1.880 | 2.050 | 1.780 | 1.820 | 1.680 | 1.720 |
| 350 | 35 | 1.870 | 2.050 | 1.820 | 1.860 | 1.680 | 1.720 |
| 400 | 40 | 1.850 | 2.050 | 1.820 | 1.860 | 1.680 | 1.720 |

The "Maximum Basis Weight" column specifies the maximum basis weight in gsm of the paper product for which the filter set should be used. The "Maximum Water Weight" column specifies the maximum water weight in gsm for which the filter set should be used. Thus, for a particular context, the customer specifies the maximum basis weight and the maximum percent moisture for the paper being manufactured and the appropriate filter sets are then selected from Table 1 which satisfy both of these conditions.

Maximum water weight can be calculated by the following equation:

maximum water weight = maximum basis weight * maximum percent moisture * 100

As previously mentioned, the infrared radiation from the infrared source 16 is sinusoidally modulated by the tines 28 of the vibrating tuning fork 26. Thus, the output of each infrared detector 36, 38 and 46 is also sinusoidally modulated at the same frequency and phase as the detected infrared beams 32, 34 and 47. However, infrared energy from the paper web 12 itself and from other external sources (not shown) will also reach the detectors 36, 38 and 42. Thus, each detector signal also includes a DC component.

The output of each of the three detectors 36, 38 and 46 is transmitted to the signal processing circuitry 52. This circuitry is designed to filter out the DC component of the detector signals. The filtered detector signals are then passed on to a phase synchronous demodulation circuit included within the signal processing circuitry 52. The purpose of the phase synchronous demodulator is to filter out changes in the signals from the detectors 36, 38 and 46, which changes are not caused by the varying infrared absorption of the web 12. For example, 60 Hz line noise in the detector signals is filtered out by the demodulator circuit, as explained below.

A sine wave oscillator 54 is used to drive the tines 28 of the tuning fork 26 at the resonant frequency of the tuning fork 26. The output of this sine wave oscillator 54 is first converted to a square wave having the same frequency and phase as the sine waves driving the tuning fork 26. This square wave output 53 is fed to the phase synchronous demodulator portion of the signal processing circuitry 52, along with the filtered signals from each of the three infrared detectors 36, 38 and 46. The signals from the infrared detectors 36, 38 and 46 are, of course, modulated at the same frequency and phase as the output of the oscillator 54. Thus, by demodulating the outputs from each detector 36, 38 and 46 with a square wave having the same frequency and phase as the output of the tuning fork oscillator 54, and then averaging the demodulated outputs over a number of cycles, the moisture sensing device 10 of the present invention filters out changes in the detector signals These changes in the detector signals result from changes in the intensity of external infrared sources, or extraneous signals such as the 60 Hz line voltage. This filtering technique using a phase synchronized demodulation circuit is well known. Changes in the intensity of the infrared energy reaching the detectors 36, 38 and 46 from other external sources or from the power line would, of course, provide an erroneous moisture content measurement.

The averaged amplitude of each of the demodulated signals from each detector is indicative of the amount of infrared transmission through the web within the pass band of the filter associated with each detector. The amplitude of these amplitude averaged and demodulated detector signals is then measured by the signal processing circuitry, digitized, and fed to the process control computer 50. This computer 50 computes the moisture content of the web 12 utilizing the equations and techniques described below. The resulting computed value of the web moisture content is indicative of the amount of moisture in the web 12, irrespective of the web temperature and basis weight.

The computer combines the digitized detector amplitude signals to achieve an output indicative of the moisture content of the web 12 according to an equation. This equation combines values indicative of the amplitudes of each of the detector signals to achieve a weighted average of these three values The weighting coefficients of the equations are dependent upon the width of the pass bands of each filter and their locations on the absorption spectrum 101. The coefficient values are chosen empirically to provide the weighted average of the detector signal values with minimal sensitivity to changes in temperature and basis weight. One presently preferred moisture calculation proceeds as follows:

A water ratio R1, which is a rough measure of the water weight per unit area of the web, is given by the following formula $R1 = REF/MES$. A second ratio R2, which is influenced by the web temperature, is calculated as: $R2 = REF/CORR$. The REF or reference value, as previously mentioned, is sensitive to the basis weight of the web, whereas the MES or measurement value is primarily sensitive to the moisture content of the web. The CORR, or temperature correction value, is dependent upon the web temperature. The ratios R1 and R2 are then combined to give a third ratio, RT, which is indicative of the amount of water in the web, but which is highly insensitive to web temperature. A preferred equation for calculating the ratio RT is provided as follows:

$$RT = R1*(1 + C1*(R2 - C2)*(1 + C3*BW + C4*R1))$$

In the above equation for RT, BW is the basis weight of the web, and C1, C2, C3 and C4 are constants which are chosen to minimize the temperature dependence of RT. R1 will be approximately equal to 1 when the web is completely dry. Similarly, R2 will be approximately equal to 1 when the web is completely dry. The value of R2 for the dry web may deviate slightly from 1, however, since the REF and CORR wavelength regions may be sufficiently separated along the wavelength spectrum that the difference in absorption of the dry paper at these two wavelengths will not be equal. Thus, by setting C2 at the value of R2 for a perfectly dry web, RT will equal R1 when the web is dry.

The optimal values for C1, C2, C3 and C4 may be determined by taking readings of the MES, REF and CORR signals using samples of a moisture-containing web which is sealed between two plates of glass. The glass serves not only to maintain constant moisture values within the paper web during the calibration measurements, but also to provide a thermal mass which maintains the temperature of the web sufficiently long enough to make possible a series of measurements at decreasing temperatures above ambient temperature. To accomplish this, the glass-enclosed web is first heated. Then, measurements of the infrared penetration through the glass-enclosed web is made periodically as the temperature decreases. By obtaining values of the ratios of R1 and R2 over a range of temperatures, the values of C1, C2, C3 and C4 can be chosen to minimize the sensitivity of RT to changes in temperature over the same range.

In the manufacture of paper, many web processing steps occur at elevated temperatures. Thus, the average web temperature at the sensor location is frequently above the ambient temperature (e.g., 100° C.). As with the previously discussed formula, C1, C2, C3 and C4 are chosen to minimize the sensitivity of RT to changes in web temperature.

The process control computer 50 can calculate the water weight per unit area from any of the above formulas using the linear equation $WW = A*RT + D$, wherein A and D are the slope and intercept, respectively, of the line defined by the linear equation, and WW is the water weight per unit area of the web.

From this latter equation, the percentage of moisture in the web can then be calculated using an auxiliary measurement of the weight per unit area of the web, BW. Thus, the percent moisture content of the web is calculated by the process control computer 50 by multiplying 100 * WW/BW.

A number of embodiments of the device of the present invention have been described With these embodiments, the process control computer of a modern automated paper mill can continuously measure the moisture content of a moving paper web at a number of locations across the length and width of the web. The moisture measurements are compensated for changes in the temperature and the basis weight of the web With these temperature and basis weight compensated moisture measurements, the paper mill process control computer can selectively activate various previously known devices for increasing and decreasing the moisture content of portions of the web to thereby produce high quality paper having a uniform moisture content. As previously mentioned, water showers and infrared lamps, for example, may be used to control the web moisture content.

From the above, one skilled in the art will understand that many modifications may be made to the optical system and the processes described herein without departing from the spirit and scope of the invention. For example, the pass bands of the filters in the receiver half of the sensor may be chosen at values other than those shown in FIGS. 2-3. Also, the equations may be changed or modified. Moreover, measurements of the infrared transmission at four or more separate wavelength regions of the infrared transmission spectrum may be made and these measurements combined in a weighted average to yield a value indicative of the web moisture content, which combination is insensitive to changes in web temperature and basis weight. Thus, the invention is not limited to the specific embodiments described herein.

I claim:

1. A web moisture sensor insensitive to web temperature, comprising:
   an infrared radiation source for directing a beam of infrared radiation through a web; and
   means for detecting the amount of infrared radiation from the beam which emerges from the web in first, second and third separate wavelength regions of the infrared spectrum, wherein the first region surrounds the infrared absorption peak for water in the web such that the amount of infrared radiation detected in the first region is substantially insensitive to the web temperature, the second region is in a part of the infrared spectrum that is less sensitive to the water in the web than the first region and is substantially insensitive to the web temperature, and the third region is in a part of the infrared spectrum which is sensitive to the web temperature.

2. The web moisture sensor of claim 1, wherein the first region is from about 1.92 to about 1.95 microns, the second region is from about 1.82 to about 1.86 microns and the third region is from about 1.68 to about 1.72 microns.

3. The web moisture sensor of claim 2, wherein the web is paper having a maximum basis weight of about 70 gsm and a maximum moisture content of about 7 gsm.

4. The web moisture sensor of claim 1, wherein the first region is from about 1.90 to about 2.00 microns, the second region is from about 1.78 to about 1.82 microns and the third region is from about 1.68 to about 1.72 microns.

5. The web moisture sensor of claim 4, wherein the web is paper having a maximum basis weight of about 150 gsm and a maximum moisture content of about 15 gsm.

6. The web moisture sensor of claim 1, wherein the first region is from about 1.88 to about 2.05 microns, the second region is from about 1.78 to about 1.82 microns and the third region is from about 1.68 to about 1.72 microns.

7. The web moisture sensor of claim 6, wherein the web is paper having a maximum basis weight o about 250 gsm a maximum moisture content of about 25 gsm.

8. The web moisture sensor of claim 1, further comprising means for calculating the web moisture content using the detected amounts of infrared radiation for each of the first, second and third regions of the infrared spectrum and using the amount of the infrared radiation detected for the third region to compensate for any difference in the temperature sensitivity of the first and second region.

9. A web moisture sensor insensitive to web temperature, comprising:
   an infrared radiation source for directing a beam of infrared radiation to a web; and
   means for detecting the amount of infrared radiation from the beam which emerges from the web in first, second and third separate wavelength regions of the infrared spectrum, wherein the first region is positioned around the infrared absorption peak for water in the web and at a part of the infrared spectrum which minimizes sensitivity to the web temperature, the second region is in a part of the infrared spectrum which is less sensitive to the water in the web than the first region and sensitive to the web temperature to substantially the same degree as the first region, and the third region is positioned at a part of the infrared spectrum which is sensitive to the web temperature.

10. The web moisture sensor of claim 9, wherein the first region is from about 1.87 to about 2.05 microns, the second region is from about 1.82 to about 1.86 microns and the third region is from about 1.68 to about 1.72 microns.

11. The web moisture sensor of claim 10, wherein the web is paper having a maximum basis weight of about 350 gsm and a maximum moisture content of about 35 gsm.

12. The web moisture sensor of claim 9, wherein the first region is from about 1.85 to about 2.05 microns, the second region is from about 1.82 to about 1.86 microns and the third region is from about 1.68 to about 1.72 microns.

13. The web moisture sensor of claim 12, wherein the web is paper having a maximum basis weight of about 400 gsm and a maximum moisture content of about 40 gsm.

14. The web moisture sensor of claim 9, further comprising means for calculating the web moisture content using the detected amounts of infrared radiation for each of the first, second and third regions of the infrared spectrum and using the amount of the infrared radiation detected for the third region to compensate for any difference in the temperature sensitivity of the first and second region.

15. A method for determining the moisture content of a web, comprising the steps of:
   (a) directing a beam of infrared radiation to the web;
   (b) measuring the amount of infrared radiation emerging from the web in first, second and third separate regions of the infrared spectrum, wherein the first region is positioned around the infrared absorption peak for moisture to minimize sensitivity to the web temperature, the second region is in a part of the infrared spectrum which is less sensitive to the moisture than the first region and sensitive to the web temperature to substantially the same degree as the first region, and the third region is positioned at a part of the infrared spectrum which is sensitive to the web temperature; and (c) calculating, with a computer, the moisture content of different portions of the web using the measurements of the infrared transmission for the first and second regions of the infrared band and compensating for temperature variations of the web using the measurements of the infrared in the third region.

16. The method of claim 15, wherein the computer calculates the moisture content using the formula:

$$RT = R1*(1 + C1*(R2 - C2)*(1 + C3*BW + C4*R1))$$

wherein
R1 = REF/MES,
R2 = REF/CORR,
C1, C2, C3 and C4 are constants, and wherein the MES value is indicative of the infrared measurement in the first region, the REF value is indicative of the infrared measurement in the second region and the CORR value is indicative of the infrared measurement in the third region and BW is the weight per unit area of the web.

17. The process of claim 16, further comprising the step of calculating, with the computer, the weight of the moisture in the web using the linear equation WW = A*RT + D, wherein A and D are the slope and the intercept of the linear equation, respectively, and WW is the moisture weight per unit area of the web.

18. A method for determining the moisture content of a web, comprising the steps of:
(a) directing a beam of infrared radiation to the web;
(b) measuring the amount of infrared radiation emerging from the web in first, second and third separate regions of the infrared spectrum, wherein the first region is positioned around the infrared absorption peak for moisture to minimize sensitivity to the web temperature, the second region is in a part of the infrared spectrum that is less sensitive to the water in the web than the first region and is substantially insensitive to the web temperature, and the third region is in a part of the infrared spectrum which is sensitive to the web temperature; and
(c) calculating, with a computer, the moisture content of different portions of the web using the measurements of the infrared transmission for the first and second regions of the infrared band and compensating for temperature variations of the web using the measurements of the infrared in the third region.

19. The method of claim 18, wherein the computer calculates the moisture content using the formula:

$$RT = R1*(1 + C1*(R2 - C2)*(1 + C3*BW + C4*R1))$$

wherein
R1 = REF/MES,
R2 = REF/CORR,
C1, C2, C3 and C4 are constants, and wherein the MES value is indicative of the infrared measurement in the first region, the REF value is indicative of the infrared measurement in the second region and the CORR value is indicative of the infrared measurement in the third region and BW is the weight per unit area of the web.

20. The process of claim 19, further comprising the step of calculating, with the computer, the weight of the moisture in the web using the linear equation WW = A*RT + D, wherein A and D are the slope and the intercept of the linear equation, respectively, and WW is the moisture weight per unit area of the web.

* * * * *